United States Patent [19]

Jost et al.

[11] Patent Number: 4,905,944
[45] Date of Patent: Mar. 6, 1990

[54] HOME CARE INTRAVENOUS STAND

[75] Inventors: George Jost, Lake in the Hills; Charles C. Tseng, Lake Bluff, both of Ill.

[73] Assignee: Baxter International Inc., Deerfield, Ill.

[21] Appl. No.: 302,708

[22] Filed: Jan. 26, 1989

[51] Int. Cl.$^4$ .............................................. A47G 29/00
[52] U.S. Cl. ....................................... 248/125; 248/129
[58] Field of Search .................... 248/121, 122, 123.1, 248/124, 125, 159, 129; 604/80, 93, 141, 245, 246; 128/DIG. 12; 211/71, 74

[56] References Cited

U.S. PATENT DOCUMENTS

| | | | |
|---|---|---|---|
| D. 287,055 | 12/1986 | Fick et al. ........................... D24/29 |
| 641,748 | 1/1900 | Smith ................................. 248/122 |
| 1,795,296 | 3/1931 | De Zeng ......................... 248/124 X |
| 2,479,720 | 8/1949 | Brandt ............................. 248/123.1 |
| 2,679,890 | 6/1954 | Zannoth ............................. 248/124 |
| 3,026,079 | 3/1962 | Stack ................................. 248/125 |
| 3,625,219 | 12/1971 | Abrams ......................... 248/125 X |
| 3,709,372 | 1/1973 | Alexander ........................... 211/74 |
| 3,709,556 | 1/1973 | Allard et al. ...................... 297/188 |
| 3,809,349 | 5/1974 | Baedke ................................ 248/51 |
| 4,045,044 | 8/1977 | Bierer ................................. 280/87 |
| 4,101,108 | 7/1978 | Klein ................................. 248/243 |
| 4,213,648 | 7/1980 | Steichen ............................ 297/188 |
| 4,225,104 | 9/1980 | Larson .............................. 248/125 |
| 4,262,872 | 4/1981 | Kodet ............................... 248/311 |
| 4,332,378 | 6/1982 | Pryor .................................. 272/70 |
| 4,410,158 | 10/1983 | Maffei ................................ 248/214 |
| 4,431,206 | 2/1984 | Pryor ................................. 280/289 |
| 4,506,903 | 3/1985 | Bowermaster ..................... 280/289 |
| 4,511,157 | 4/1985 | Wilt, Jr. ............................. 280/289 |
| 4,511,158 | 4/1985 | Varga et al. ....................... 280/292 |
| 4,572,536 | 2/1986 | Doughty ........................... 280/289 |
| 4,602,755 | 7/1986 | Rosten .............................. 248/214 |
| 4,640,521 | 2/1987 | Berfield ........................ 248/129 X |
| 4,648,144 | 3/1987 | Rose .................................... 5/503 |
| 4,657,249 | 4/1987 | Offutt ............................. 273/1.5 R |
| 4,691,397 | 9/1987 | Netzer ................................. 5/507 |
| 4,696,420 | 9/1987 | Kulik ................................ 224/275 |
| 4,706,368 | 10/1987 | Crissman, III et al. ............. 29/526 |
| 4,725,027 | 2/1988 | Bekanich .......................... 248/125 |
| 4,729,576 | 3/1988 | Roach ............................... 280/493 |
| 4,744,536 | 5/1988 | Bancalari ......................... 248/125 |
| 4,767,131 | 8/1988 | Springer et al. .................. 280/289 |

Primary Examiner—J. Franklin Foss
Attorney, Agent, or Firm—Paul E. Schaafsma; Susan B. Fentress; Paul C. Flattery

[57] ABSTRACT

A stable and highly maneuverable home care intravenous container stand is provided. The present device includes a base defining a low center of gravity which is supported by front casters and back wheels. A main pole is removably retained in a clamp secured to the base. An adjustable sub-pole having a support arm is telescopically carried to the main pole. A vertically adjustable handle is provided on the main pole.

10 Claims, 4 Drawing Sheets

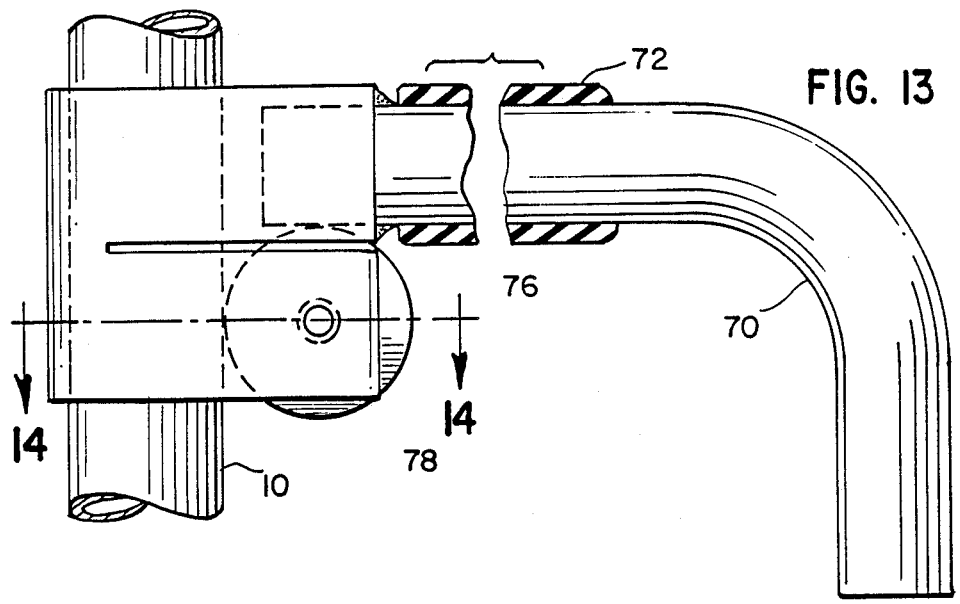
FIG. 13
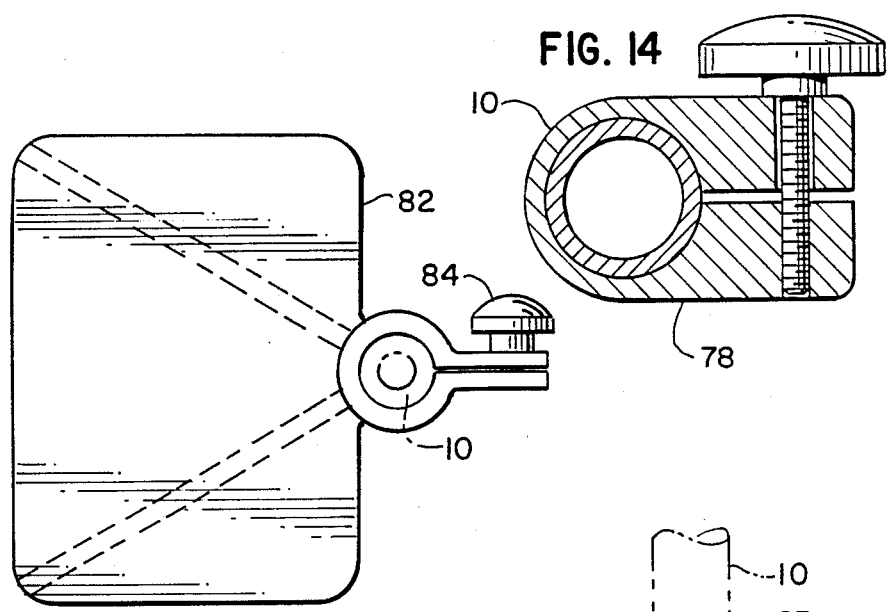
FIG. 14
FIG. 15
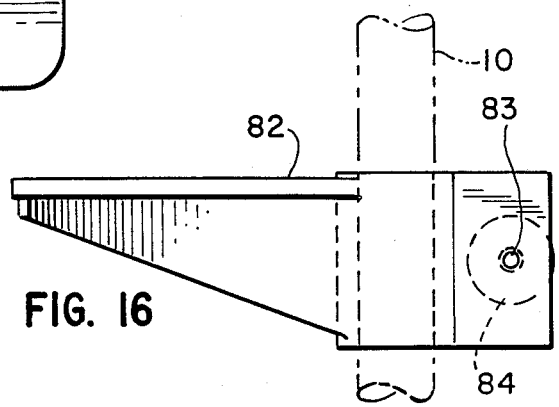
FIG. 16

HOME CARE INTRAVENOUS STAND

BACKGROUND OF THE INVENTION

Flexible containers containing intravenous solutions and equipment to administer these solutions to patients are generally held on a vertically displaced pole secured to a stand. It has been recognized that patients should be ambulatory and, thus, able to move the pole supporting the I.V. materials. Certain ambulatory patient stands have been devised. For example, U.S. Pat. No. 4,323,378 discloses a stand with a torodial ring grip and wheels; however, for home care this stand does not provide sufficient maneuverability. In the home care situation, a patient will need to move the pole supporting the I.V. materials up and down stairs and around many objects. In order to obtain this desired maneuverability, patients have adapted objects, such as golf carts, to hold I.V. associated materials. These adapted golf carts, however, do not provide the stability needed to hold flexible containers and pumps.

It is, therefore, desirable to provide a light weight intravenous stand that is both maneuverable and stable for home care use, and can be easily assembled and disassembled for easy storage and transportation.

SUMMARY OF THE INVENTION

The present invention overcomes the disadvantages and deficiencies noted with respect to the prior home care stands by providing a stable, light weight maneuverable home intravenous stand.

The present invention includes a base supported by front casters and back wheels. The base defines a low center of gravity to increase device stability. A main pole is removably retained in a clamp secured to the base to provide ease in assembling and disassembling the device. An adjustable sub-pole having an arm to carry the solution containers is telescopically carried in the main pole and secured thereto by a clamp. Thus, the height of the solution containers can be adjusted. Finally, a height adjustable handle is contained on the main pole to accommodate patients of different heights.

BRIEF DESCRIPTION OF THE DRAWINGS

FIG. 13 is a side elevational, partially sectional view of main pole, knob and adjustable handle of the device of FIG. 1.

FIG. 14 is a top sectional view of main pole and adjustable handle of the device of FIG. 1.

FIG. 15 is a top view of an optional infusion pump platform in accordance with the principles of the present invention.

FIG. 16 is a side elevational view of the infusion pump platform of FIG. 15.

DETAILED DESCRIPTION OF A PREFERRED EMBODIMENT

Figures 1, 2:
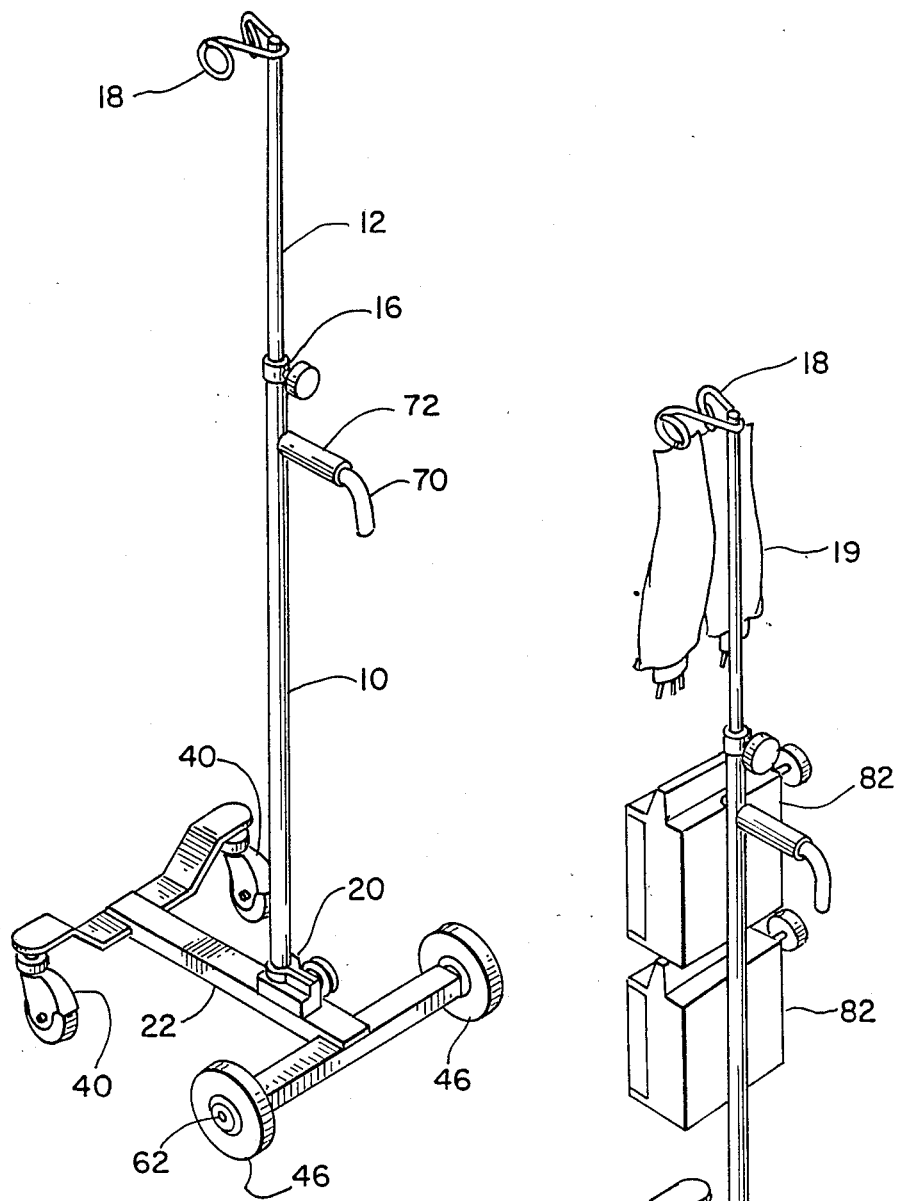
FIG. 1 is a view showing the home care I.V. stand.
FIG. 2 is a perspective view of the home care I.V. stand of FIG. 1 equipped with I.V. solution containers and infusion pumps.

Referring now to the drawings therein is illustrated a home care I.V. stand constructed in accordance with the principles of the present invention.

Referring particularly to FIG. 1, a base 8 is supported by two (2) castered wheels 40 and two (2) neoprene wheels 46. A clamp 20 is affixed to base 8. Clamp 20 releasably grips a main pole 10 which extends vertically from base 8. A handle 70 having a grip enhancing material such as a rubber sleeve 72 is carried on the main pole 10. A sub-pole 12 telescopically extends from main pole 10. The height of sub-pole 12 is adjusted by knob 16. A pair of arms 18 adapted to secure the parenteral solution container 19 is affixed to the top of sub-pole 12.

Referring to FIG. 2 the home care I.V. stand of FIG. 1 is seen in use. The parenteral solution containers 19 are hung on arms 18 and infusion pumps 82 are supported by platforms attached to the main pole 10 and fastened to the main pole 10 by the pole clamps.

Figure 3:
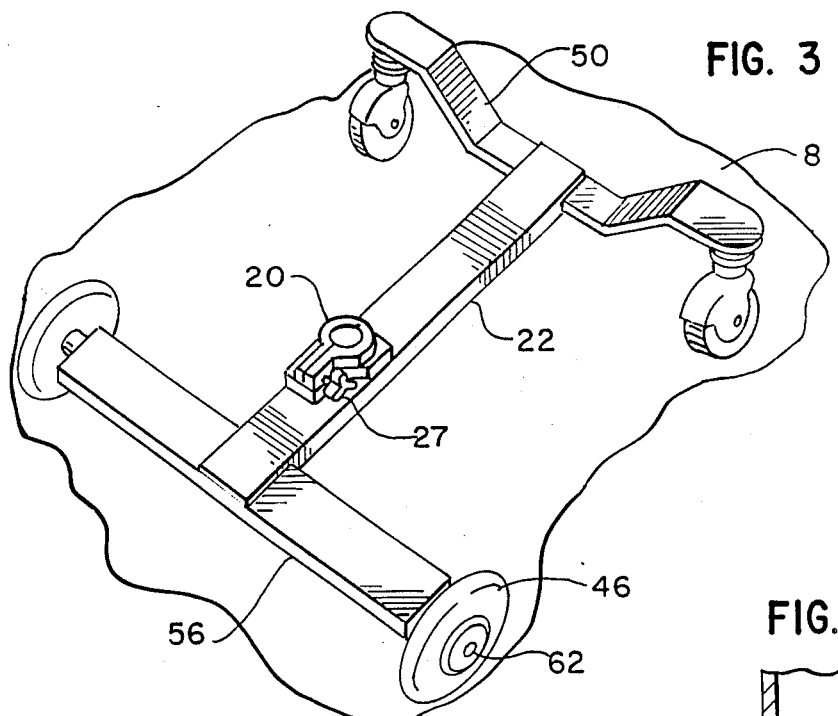
FIG. 3 is a perspective view of the platform base and clamp of the device of FIG. 1.

Referring to FIG. 3, base 8 is comprised of base weldment 22 having clamp 20 affixed on top, front caster housing 50 and back wheel housing 56.

Figure 5:
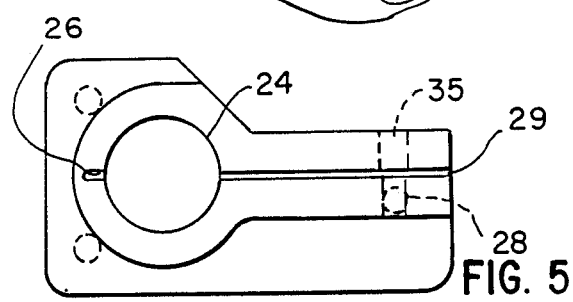
FIG. 5 is a top view of the clamp of the device of FIG. 1.
Figure 4:
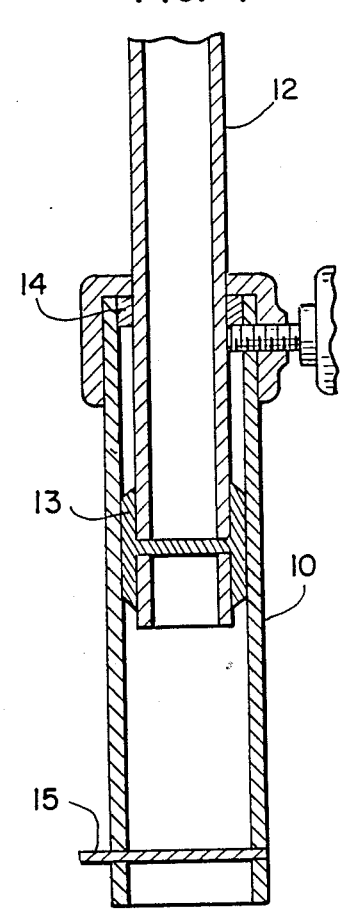
FIG. 4 is a sectional front view of the fitting associating the main pole and sub-pole of the device of FIG. 1.

FIG. 4 shows the fitting associating main pole 10 and sub-pole 12. Sub-pole 12 has a ring 13 attached at its lower end while main pole 10 has a flange 14 on at its upper end. Flange 14 in conjunction with ring 13 prevents sub-pole 12 from disassociating with main pole 10. The ring 13 also prevents sub-pole 12 from rattling inside the main pole 10. A pin 15 is provided near the lower end of the main pole 10 which slips into and is retained in a notch 26 defined in clamp 20, as best seen in FIG. 5. This pin 15 and notch 26 association helps assemble the main pole 10 in proper direction and also prevent the main pole 10 from rotation.

Clamp 20 defines a cylindrical aperture 24 which includes notch 26. Screw knob 27 is releasably held in screw hole 28. A cut 29 runs from the end of the clamp 20 to the cylindrical hole 24, and separate clearance hole 35 is provided from the screw hole 28 so that screw knob 27 can secure clamp 20.

Figure 6:
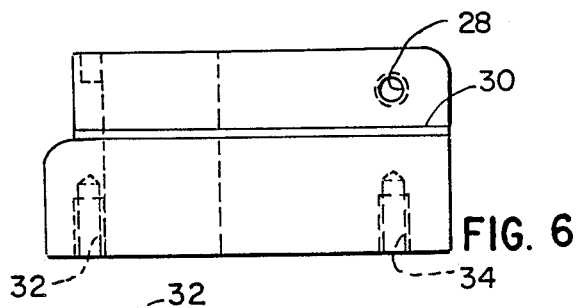
FIG. 6 is a side elevational view of the clamp of FIG. 5.

Referring to FIG. 6, a side elevational view of the clamp 20 is seen showing horizontal cut 30 and screw holes 28, 32 and 34.

Figure 7:
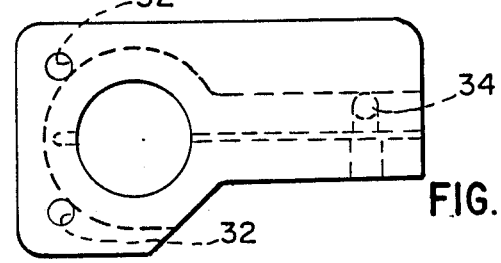
FIG. 7 is a bottom view of the clamp of FIG. 5.

FIG. 7 shows a bottom view of clamp 20. Also depicted are screw holes 32, 34 and the bottom of cylindrical hole 24.

Figure 8:
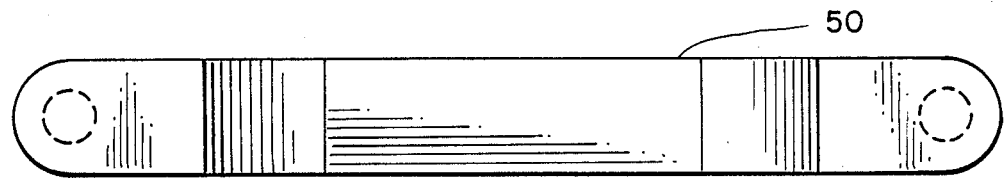
FIG. 8 is a top view of the front caster housing of the platform base of the device of FIG. 1.
Figure 9:
FIG. 9 is a front elevational view of the front caster housing of the platform base of FIG. 8.
Figure 11:
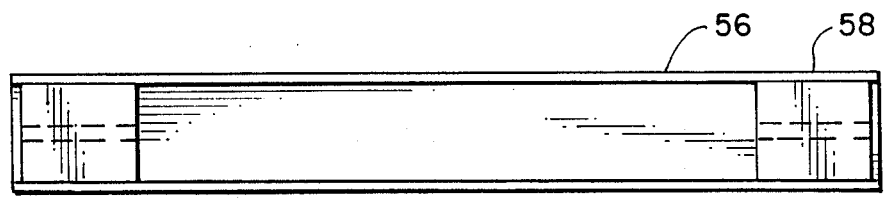
FIG. 11 is a top view of the rear wheel housing of the platform base of the device of FIG. 1.

Referring now to FIGS. 8 and 9, front caster housing 50 is seen. The middle section of the front caster housing is lower to provide a low center of gravity for the housing. The middle section remains the same height as the wheel housing 56, as seen in FIG. 11. The front caster housing is bent upwardly to receive casters 40. The casters are attached to the housing by tube 52.

Figure 10:
FIG. 10 is a side elevational view of the base weldment connecting the front caster housing and rear wheel housing of the device of FIG. 1.

Referring to FIG. 10, a side elevational view of base weldment 22 is seen. Base weldment 22 is adapted to be secured and connect front caster 50 and rear wheel 56 housings.

Figure 12:
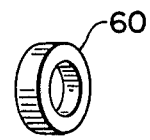
FIG. 12 is a perspective view of the rear wheel spacers of the device of FIG. 1.

Referring particularly to FIG. 11, FIG. 11 shows rear wheel housing 56 welded to block 58, to which plastic spacer 60 is attached. Wheel 46 is attached through round head screw 62 to the block through spacer 60. (See FIG. 12).

Referring to FIGS. 13 and 14, the handle adjustment clamp 74 is seen in detail. Clamp 74 includes a cylinderical hole 73 through which main pole 10 extends, notch 76, and bearing knob 78.

The handle 70 is securely attached by welding to adjustable handle clamp 74. The adjustable handle clamp 74 provides for vertical alignment of handle 70 on main pole 10. As previously seen, a portion of handle 70 is covered with a rubber sleeve 72 to enhance user gripping.

The optional infusion pump platform 82 is removably secured to the main pole 10, as seen in FIG. 15. The infusor pump platform 82 includes a platform 82 and pole clamp 84.

FIG. 16 shows a side elevational view of the infusion pump platform 82 and screw hole 83 for pole clamp 84.

It should be understood that various changes and modifications to the preferred embodiment described herein will be apparent to those skilled in the art. Such changes and modifications can be made without departing from the spirit and scope of the present invention and without diminishing its attendant advantages. It is therefore intended that the scope of the patent be defined by the appended claims.

What is claimed is:

1. A light weight, maneuverable and stable home care intravenous stand having a main pole and a sub-pole nonremovably associated with said main pole comprising:
   (a) a base having a back and a front, said base supported by front base casters and back base wheels, said base defining a center of gravity of said stand below the top of said base wheels;
   (b) a clamp affixed to said base, said clamp adapted to removably retain said main pole;
   (c) said main pole having a vertically adjustable handle; and
   (d) said sub-pole being telescopically associated with said main pole and having an arm affixed to said sub-pole adapted to support at least one intravenous solution container.

2. The home care I.V. stand of claim 1 wherein said sub-pole is height adjustable.

3. The home care I.V. stand of claim 1 wherein said main pole is aligned in said clamp affixed to said base by a pin on said main pole that is received by a notch defined in said clamp.

4. The home care I.V. stand of claim 1 wherein the sub-pole is prevented from disassociating with said main pole by a flange member attached to the inside of said main pole.

5. A light weight, maneuverable and stable home care intravenous stand having a main pole and a sub-pole nonremovably associated with said main pole comprising:
   (a) a base having a back and a front, said base supported by front base casters and back base wheels, said base defining a center of gravity of the said stand below the top of said base wheels;
   (b) a clamp affixed to said base, said clamp adapted to removably retain said main pole;
   (c) said main pole having a vertically adjustable handle and a vertically adjustable infusion pump platform attached to said main pole; and
   (d) said sub-pole being telescopically associated with said main pole and having an arm affixed to said sub-pole adapted to support at least one intravenous solution container.

6. The home care I.V. stand of claim 5 wherein said sub-pole is height adjustable.

7. The home care I.V. stand of claim 5 wherein said main pole is aligned in said clamp affixed to said base by a pin on said main pole that is received by a notch defined in said clamp.

8. The home care I.V. stand of claim 5 wherein the sub-pole is prevented from disassociating with said main pole by a flange member attached to the inside of said main pole.

9. The home care I.V. stand of claim 5 wherein the nonremovable sub-pole is prevented from rattling inside said main pole by attaching a ring to said sub-pole at the lower end.

10. A home care intravenous stand comprising:
   a base having a clamp, the base being maneuverable on a pair of casters and a pair of wheels attached thereto, the wheels defining a bottom rolling surface and a top opposite the bottom surface, the base defining a center of gravity of the stand below the top of the wheels;
   a main pole removably secured in the clamp;
   a vertically adjustable handle secured to the main pole; and
   a sub-pole telescopically associated with the main pole.

* * * * *